United States Patent
Byrne et al.

[11] Patent Number: 5,156,849
[45] Date of Patent: Oct. 20, 1992

[54] PHARMACEUTICAL COMPOSITION

[75] Inventors: William Byrne, Dublin; Andrew Rynne, Clane; Olive Corrigan, Dublin, all of Ireland

[73] Assignee: Byrne Rynne Holdings Limited, Clane, Ireland

[21] Appl. No.: 661,848

[22] Filed: Feb. 26, 1991

[30] Foreign Application Priority Data

Feb. 26, 1990 [IE] Ireland .................. 675/90

[51] Int. Cl.⁵ ..................... A61K 9/62
[52] U.S. Cl. .................. 424/451; 424/456; 424/461; 424/480
[58] Field of Search .......... 424/451, 465, 463, 464, 424/480; 514/822, 922

[56] References Cited

U.S. PATENT DOCUMENTS

| 2,965,541 | 12/1976 | Byrnes | 424/451 |
| 4,315,924 | 2/1982 | Perrot | 424/233 |
| 4,464,377 | 8/1984 | Blanchard et al. | 514/822 |
| 4,693,896 | 9/1987 | Wheatley | 424/480 |
| 4,695,466 | 9/1987 | Morishita et al. | 424/451 |
| 4,798,811 | 1/1989 | Lehmann et al. | 514/159 |
| 5,032,406 | 7/1991 | Dansereau et al. | 424/465 |

FOREIGN PATENT DOCUMENTS

| 0029790 | 6/1981 | European Pat. Off. |
| 103991 | 3/1984 | European Pat. Off. |
| 117164 | 8/1984 | European Pat. Off. |
| 0219728 | 4/1987 | European Pat. Off. |
| 2319346 | 2/1977 | France |
| 2368272 | 5/1978 | France |
| 908282 | 10/1962 | United Kingdom |
| 1037689 | 8/1966 | United Kingdom |
| 1116438 | 6/1968 | United Kingdom |
| 1204580 | 9/1970 | United Kingdom |
| 1276089 | 6/1972 | United Kingdom |
| 1546448 | 5/1979 | United Kingdom |
| 2041222 | 9/1980 | United Kingdom |
| 2203338 | 10/1988 | United Kingdom |

OTHER PUBLICATIONS

Chemical Abstracts, vol. 98, May 1983, p. 375 185576g.
European Search Report.
United Kingdom Search Report.
Drug Facts & Comparisons ed. Covington, et al. Lipincott 1990 pp. 999,1003,1015.
Principles of Medicinal Chemistry, Foye, 1976, p. 540.
PDR, 1985 pp. 650,651,1802.

Primary Examiner—Thurman K. Page
Assistant Examiner—Neil S. Levy
Attorney, Agent, or Firm—Scully, Scott, Murphy & Presser

[57] ABSTRACT

A pharmaceutical product preferably in the form of a capsule comprises in one case Atenolol and aspirin. A barrier film coating including a dihydric alcohol is provided around a tablet of Atenolol which in turn is surrounded by Aspirin inside a capsule. Aspirin is preferentially and maximally absorbed in the first hour after ingestion before significant release and absorbtion of Atenolol.

13 Claims, 3 Drawing Sheets

PHARMACEUTICAL COMPOSITION

The invention relates to a pharmaceutical composition.

According to one aspect of the invention there is provided a pharmaceutical composition comprising:
a pharmaceutically active salicylate or a salt, ester, derivative, complex thereof, or salts of the ester, derivative or complex;
a second pharmaceutically active ingredient; and
a barrier between the salicylate and the second active ingredient to substantially prevent interaction therebetween in the composition.

The use of a barrier substantially prevents interaction between the active ingredients and degradation of the composition. Thus, a chemically and physically stable dosage form is provided.

In a preferred embodiment of the invention the barrier includes cellulosic material.

Advantageously, the barrier includes as a plasticiser a pharmaceutically acceptable alkyl mono or poly alcohol or ether which is compatible with the active ingredients.

In a preferred embodiment of the invention the plasticiser comprises a glycol, most preferably propylene glycol. This composition is especially advantageous as it provides a barrier film coating which contains as a plasticiser a material which is compatible with salicylates and produces an especially chemically and physically stable dosage form.

In a particularly preferred embodiment of the invention the second active ingredient comprises an anti-hypertensive agent, such as a β-blocker, most preferably Atenolol.

The salicylate may be present in a powder or granular form.

Advantageously, the salicylate comprises Aspirin which may be present in any desired form. One complex which may be preferred for ease of solubility is the complex of calcium aspirinate and urea.

In a particularly preferred embodiment of the invention the salicylate comprises aspirin, the second active ingredient comprises Atenolol, and the weight ratio of aspirin to Atenolol in the composition is from 1:2 to 6:1, most preferably approximately 3:1.

In another aspect the invention provides a pharmaceutical composition comprising a single dose combination product of an anti-platelet agent and an anti-hypertensive agent.

Most preferably the anti-platelet agent comprises a salicylate or a salt, ester derivative, complex thereof, or a salt of the ester, derivative or complex, especially aspirin which may be in any suitable physical form such as a powder or granules and may be present in any desired chemical form such as, for ease of solubility, a complex of calcium aspirinate and urea.

In one embodiment of the invention the anti-hypertensive agent comprises a β-blocker, most especially Atenolol.

In a particularly preferred embodiment of this aspect of the invention a barrier is provided between the anti-hypertensive agent and the salicylate. In one arrangement the barrier includes cellulosic material.

Particularly preferred is a barrier which includes as a plasticiser a pharmaceutically acceptable alkyl mono or poly alcohol or ether which is compatible with the salicylate, most preferably a glycol, especially propylene glycol.

Preferably, the barrier is provided around the anti-hypertensive agent.

In an especially preferred embodiment of this aspect of the invention the composition is in a form suitable for oral administration, most preferably in the form of a capsule.

Advantageously, the anti-hypertensive agent is in the form of a tablet, a barrier is provided around the tablet and the anti-platelet agent surrounds the tablet in the capsule.

In a preferred embodiment of the invention the anti-platelet agent comprises Aspirin, the anti-hypertensive agent comprises Atenolol, and the weight ratio of Aspirin to Atenolol is from 1:2 to 6:1, most preferably approximately 3:1.

In one particular aspect the invention provides a capsule containing Atenolol, aspirin, and a barrier around the Atenolol to substantially prevent interaction in the composition between the aspirin and Atenolol, the barrier comprising propylene glycol and cellulosic material, and the weight ratio of Aspirin to Atenolol in the composition being approximately 3:1.

The invention will be more clearly understood from the following embodiments thereof given by way of example only with reference to the accompanying drawings.

EXAMPLE 1

A capsule according to the invention was formulated as follows:

A. ATENOLOL TABLET

The following amounts of Atenolol and excipients and vehicles were mixed together and the mixture thus formed was compressed in a tablet press to form tablets which were approximately 6 mm in diameter, approximately 2.5 mm to 3 mm thick and weighed approximately 80 mg.

Quantities for 1,000 tablets
Atenolol: 50.0 g
Maize Starch: 4.0 g
Microcrystalline Cellulose: 21.2 g
Sodium Starch Glycolate: 4.0 g
Magnesium Stearate: 0.8 g
Distilled Water: minimum amount required.

The maize starch is added to warmed distilled water and boiled water is added to the solution thus formed and mixed. The Atenolol and Microcrystalline Cellulose are mixed and the starch solution is then added until a granulate is formed which is then dried and sieved. The Sodium Starch Glycolate is then added followed by the Magnesium Stearate. Tablets are then formed by a tabletting machine by conventional techniques.

B. COATING MATERIAL

The coating material used was a cellulosic material (a pharmaceutically acceptable alkyl cellulose derivative) using proplyene glycol as plasticiser. The solvent may be aqueous or organic. The Atenolol tablet of A was coated with this coating material by conventional techniques.

C. ASPIRIN 150 mg of granulated aspirin such as type RC3 available from Rhone Poulenc was used for each capsule.

D. CAPSULE

The capsule is of a conventional capsule material such as hard gelatin material.

COMBINATION PRODUCT

An 80 mg Atenolol tablet from A. coated with the coating material of B was placed in the capsule of D and surrounded by the granulated aspirin of C.

Figure 1:
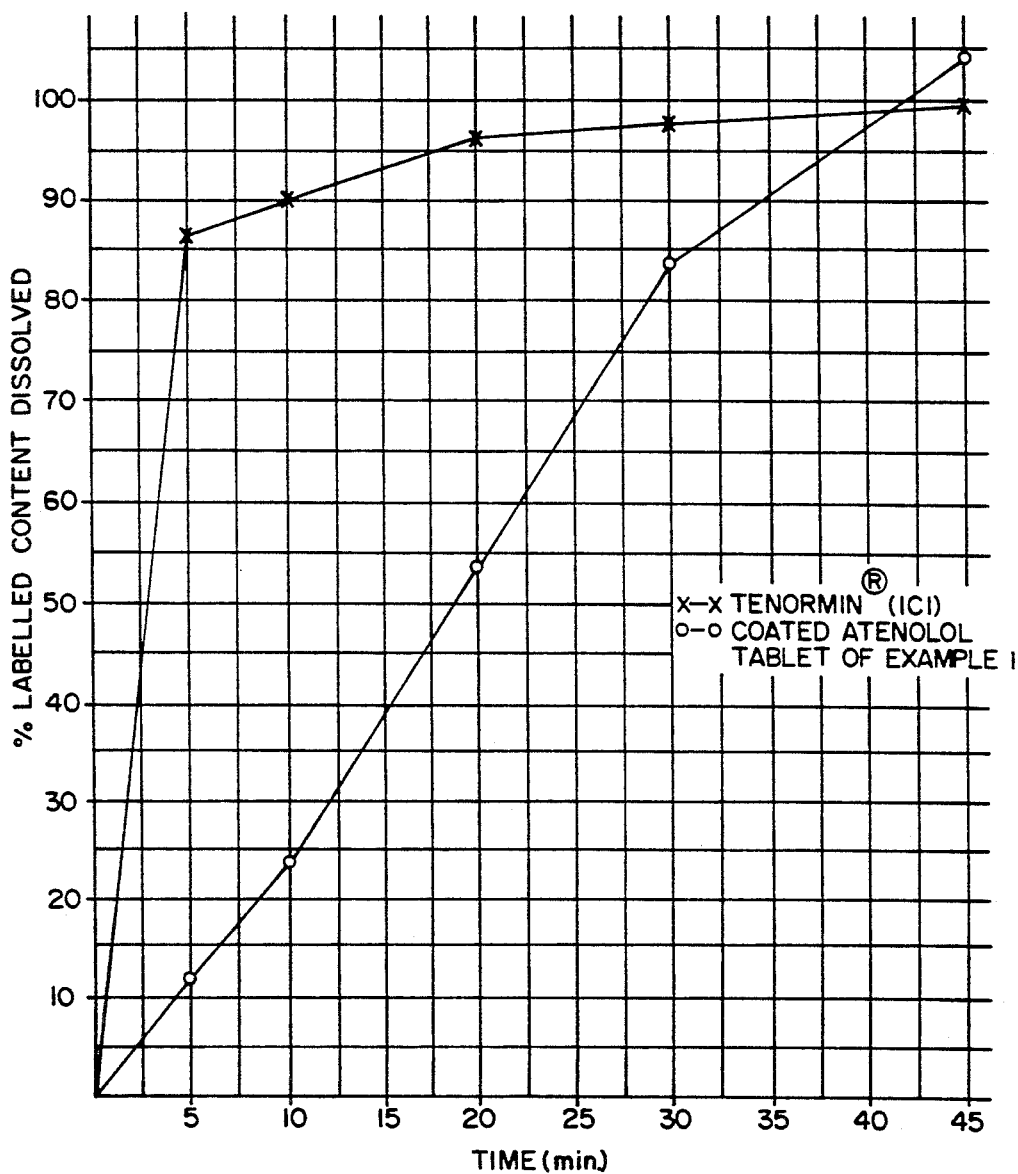
FIG. 1 is a graph of in-vitro dissolution over time of an Atenolol tablet used in one composition of the invention in comparison with a commercially available Atenolol tablet.
Figure 2:
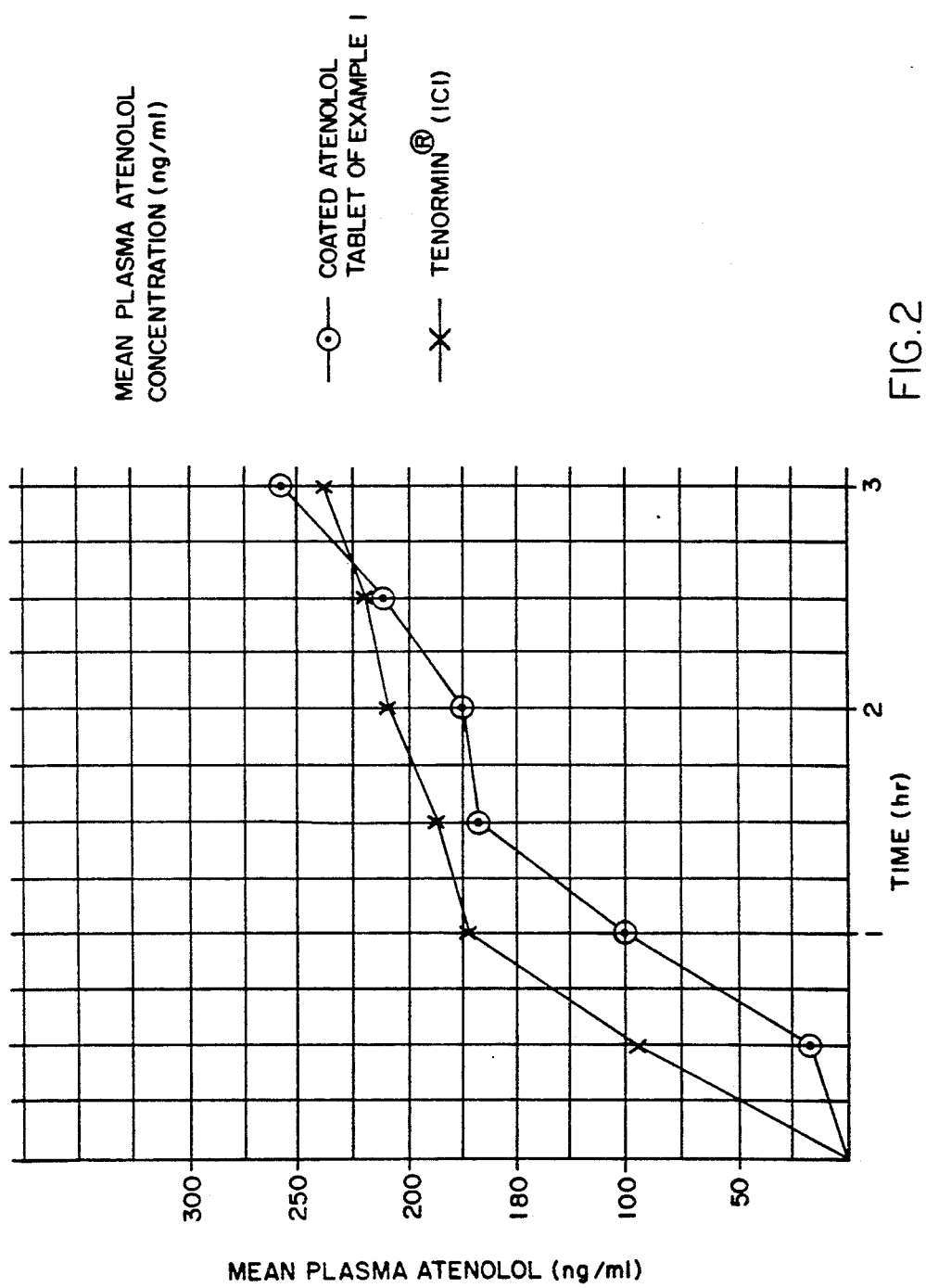
FIG. 2 is a graph of in vivo absorbtion over time of an Atenolol tablet used in one composition of the invention in comparison with the absorbtion of a commercially available Atenolol tablet over an initial 3 hour period.

To monitor the in vitro and in vivo properties of the coated Atenolol tablets, of the composition of the invention and conventional Atenolol tablets [TENORMIN (registered trade mark of ICI)] the tablets were first tested in vitro and the results are plotted in FIG. 1. Tests for absorption in vivo was also carried out and the results are plotted in FIGS. 2 and 3. FIG. 2 is on an expanded scale to FIG. 3.

Figure 3:
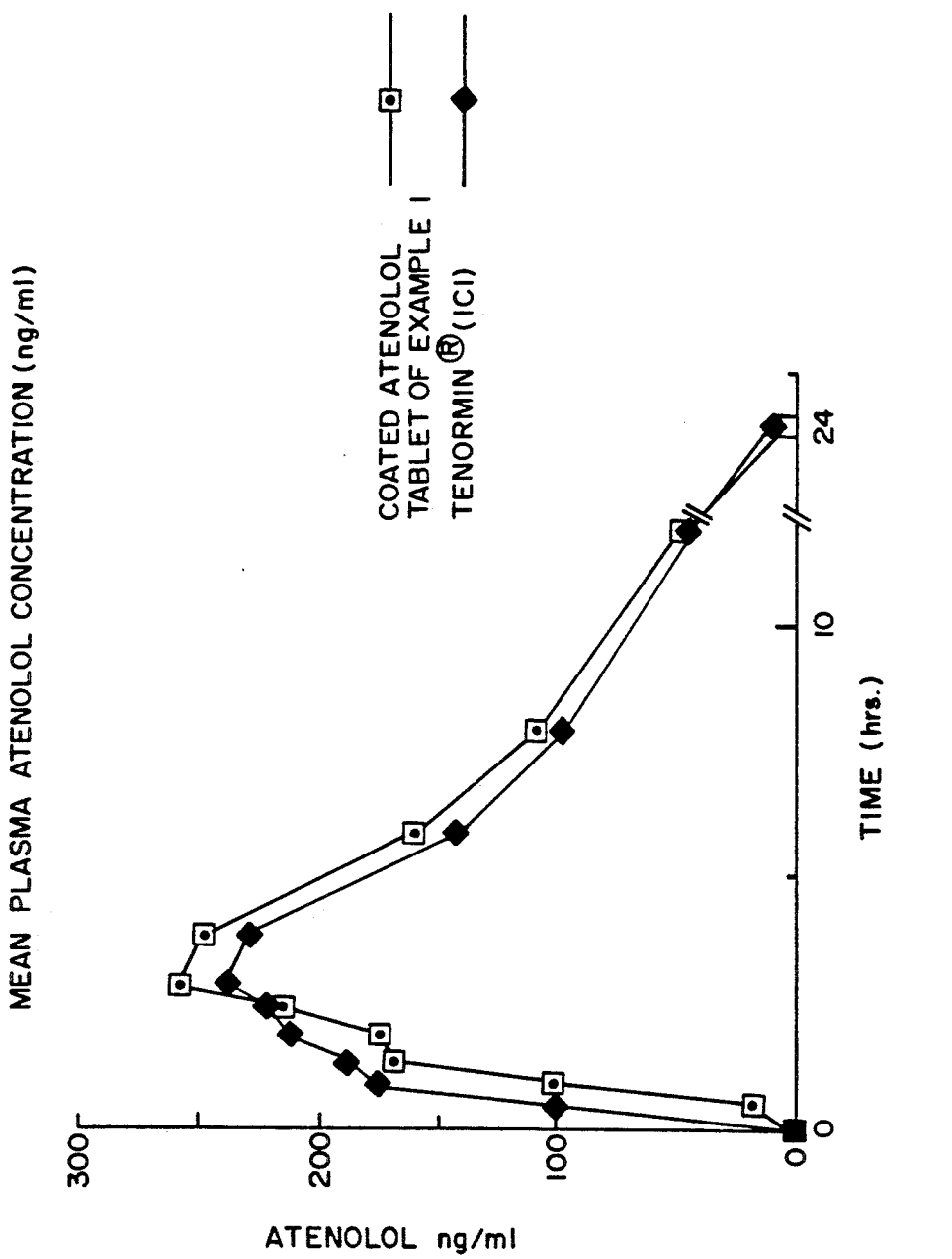
FIG. 3 is a graph of in vivo absorbtion over time of an Atenolol tablet used in one composition of the invention in comparison with the absorbtion of a commercially available Atenolol tablet over a 24 hour period.

As will be apparent from FIGS. 1, 2 and 3, the Atenolol tablet used in the composition of the invention differs from conventional Atenolol tablets as regards drug release characteristics. The retarded initial release of Atenolol is demonstrated in vitro in FIG. 1 and is reflected in the significant time delay or lag in the onset of absorption in vivo as will be apparent from FIGS. 2 and 3. Consequently, the more rapidly absorbed aspirin is preferentially and maximally absorbed in the first half hour after ingestion of the capsule of the Example above, at a time before significant release and absorption of Atenolol.

Further in vivo data was obtained for the combination product of Example 1. This data demonstrated that a time lag was sustained in the presence of asprin. The aspirin absorption was much more rapid as reflected by the peak plasma level for Aspirin which occurred approximately at ½ hour to one hour after administration.

The dissolution and absorption time lag of the Atenolol used in the composition of the invention is exploited to facilitate absorption of the asprin. Thus, the bioavailability of both drugs is optimised.

Any possibility of adverse interaction in vivo arising on concomitant release of both drugs in the gastrointestinal tract is also avoided. Thus, the release/dissolution and absorption of aspirin occurs first and to a substantial extent before the release and absorption of Atenolol thereby reducing the likelihood of in vivo adverse effects or patient injury.

Further, in medical practice, the composition of the invention has the considerable advantage of providing a single dose pharmaceutical product which combines anti-platelet action and anti-hypertensive action. As a single product only is required the product is particularly advantageous from the point of view of compliance.

Very many variations on the specific embodiments of the aspects of the invention described above will be apparent.

For example, it will be apparent that it may be possible to apply the invention to any combination products which contain aspirin (in it's various physical and chemical forms) and other drug entities which need not necessarily be anti-hypertensive agents.

In the case where the composition includes an anti-hypertensive agent this may not be restricted to Atenolol [4-[2-Hydroxy-3-[-(1-methylethyl)amino]propoxy]-benzeneacetamide in particular or β-blockers [$β_1$-adrenergic receptor blocking agents] in general. Other anti-hypertensive agents such as calcium antagonists, and ACE-inhibitors may be used as alternatives.

It will be appreciated that pharmaceutically acceptable mono or poly alcohols or ethers such as glycols other than propylene glycol may also possibly be used in the barrier film.

The particular barrier film coating will depend on the active ingredients present in the pharmaceutical composition of the invention and the mode of administration envisaged. Because Atenolol is a drug of low bioavailability, a relatively short time delay is provided by the specific barrier film coating described above to ensure no loss in bioavailability. In the case of other drugs, a more substantial time lag may be possible to accommodate and achieve by modifying the barrier coating. It may be possible to use conventional enteric coatings such as shellac, cellulose acetate phthalate and derivatives thereof, EUDRAGIT TM, polymethacrylates and the like.

The invention is not limited to the embodiments hereinbefore described which may be varied in detail.

We claim:

1. A pharmaceutical composition comprising:
a pharmaceutically active salicylate or a salt, ester, derivative, complex thereof, or salts of the ester, derivative, or complex;
Atenolol; and a barrier between the salicylate and Atenolol, the barrier comprising a cellulosic material and a plasticiser, the plasticiser comprising a pharmaceutically compatible alkyl mono or poly alcohol or ether.

2. A composition as claimed in claim 1 wherein the salicylate comprises Aspirin and the weight ratio of Aspirin to Atenolol in the composition is from 1:2 to 6:1.

3. A composition as claimed in claim 1 wherein the plasticiser comprises a glycol which is compatible with the salicylate and Atenolol.

4. A composition as claimed in claim 3 wherein the glycol is propylene glycol.

5. A composition as claimed in claim 1 wherein the barrier is provided around the Atenolol.

6. A composition as claimed in claim 1 wherein the composition is in a form suitable for oral administration.

7. A composition as claimed in claim 6 wherein the composition is in the form of a capsule containing the salicylate, Atenolol and the barrier.

8. A composition as claimed in claim 7 wherein the Atenolol is in the form of a tablet, the barrier being provided around the tablet and the salicylate surrounds the tablet in the capsule.

9. A composition as claimed in claim 2 wherein the weight ratio of Aspirin to Atenolol is approximately 3:1.

10. A composition as claimed in claim 1 wherein the salicylate is present in a powder or granular form.

11. A composition as claimed in claim 1 wherein the salicylate comprises aspirin.

12. A composition as claimed in claim 1 wherein the salicylate comprises a complex of calcium aspirinate and urea.

13. A capsule containing Atenolol, Aspirin, and a barrier around the Atenolol to prevent interaction between the Aspirin and Atenolol, the barrier comprising propylene glycol and cellulosic material, and the weight ratio of Aspirin to Atenolol in the capsule being approximately 3:1.

* * * * *